United States Patent [19]

Masamoto et al.

[11] Patent Number: 4,967,014

[45] Date of Patent: Oct. 30, 1990

[54] PROCESS FOR PRODUCING FORMALDEHYDE AND DERIVATIVES THEREOF

[75] Inventors: Junzo Masamoto; Junzo Ohtake, both of Okayama; Mamoru Kawamura, Saitama, all of Japan

[73] Assignee: Asahi Kasei Kogyo Kabushiki Kaisha, Osaka, Japan

[21] Appl. No.: 305,596

[22] Filed: Feb. 3, 1989

[30] Foreign Application Priority Data

Feb. 3, 1988 [JP] Japan ................................. 63-21872

[51] Int. Cl.$^5$ ...................... C07C 45/32; C07C 45/37
[52] U.S. Cl. .................................... 568/458; 568/470
[58] Field of Search ............................... 568/470, 458

[56] References Cited

U.S. PATENT DOCUMENTS

| | | | |
|---|---|---|---|
| 2,467,223 | 4/1949 | Payne | 568/470 |
| 4,439,624 | 3/1984 | Lewis et al. | 568/470 |
| 4,442,307 | 4/1984 | Lewis et al. | 568/470 |

FOREIGN PATENT DOCUMENTS 0134432 8/1982 Japan ................................. 568/458

OTHER PUBLICATIONS

Walker, "Formaldehyde", American Chemical Society Monograph Series Reinhold Publishing Corp., (1967), pp. 264–267.

*Primary Examiner*—Werren B. Lone
*Attorney, Agent, or Firm*—Sughrue, Mion, Zinn, Macpeak & Seas

[57] ABSTRACT

A process for formaldehyde production is disclosed comprising the steps of reacting methanol with formaldehyde to form methylal and then oxidizing the resulting methylal to obtain formaldehyde. Formaldehyde derivatives may also be produced. A dilute formaldehyde solution resulting from recovery of the product is recycled and used as feed material for the initial reaction step.

17 Claims, 4 Drawing Sheets

PROCESS FOR PRODUCING FORMALDEHYDE AND DERIVATIVES THEREOF

FIELD OF THE INVENTION

The present invention relates to a continuous process for producing formaldehyde or its derivatives from methanol. More particularly, it relates to a process for formaldehyde production which comprises the steps of reacting methanol with formaldehyde to form methylal, then oxidizing the resulting methylal to obtain formaldehyde. The present invention also relates to a process for producing derivatives of formaldehyde.

BACKGROUND OF THE INVENTION

Formaldehyde has conventionally been produced on an industrial scale by oxidizing methanol in the presence of oxidation catalysts such as silver or iron-molybdenum catalyst.

A process has also been proposed in which formaldehyde is produced by oxidizing methylal in the presence of methanol oxidation catalysts of the types described above (U.S. Pat. No. 2,467,223).

A method is also known that produces methylal by reaction between methanol and formaldehyde as described in JP-B-40-15005 (the term "JP-B" as used herein means an "examined Japanese patent publication").

Conventional methods of producing formaldehyde by oxidation of methanol have low utilization of methanol due to the formation of a large quantity of water during the reaction. In addition, the maximum concentration of the aqueous formaldehyde solution that can be thus produced is only 55 wt % and it has been difficult to obtain higher concentrations.

The formaldehyde produced by these methods is used in the manufacture of polyacetal resins, formaldehyde resins, phenol-formaldehyde resins, etc. or as a starting material for the production of paraformaldehyde, urea compounds, etc. In these applications, the concentration of formaldehyde (in the case of formalin, the concentration of formaldehyde in aqueous solution) must be as high as possible, namely, the concentration of the product formaldehyde must be increased. To meet this need, various methods have been employed including distillation or scrubbing, or alternatively, formaldehyde is first reacted with an alcohol to form hemiacetal, which then is evaporated by heating to obtain a formaldehyde-rich gas.

When highly concentrated formaldehyde is to be obtained, formaldehyde of low concentration (e.g. formaldehyde of high water content) produced by conventional means is usually unsuitable for use unless it is re-concentrated by distillation or an other appropriate method. The comparatively rigorous conditions of distillation for concentration of dilute formaldehyde to a useful level requires substantial energy consumption. In addition, distillation towers and other units in the system have to be made of special corrosion-resistant materials.

In some instances, formaldehyde is converted to derivatives thereof before it is put to the various use mentioned above. In the case of manufacturing polyacetal copolymers, formaldehyde is first converted to trioxane (a derivative of formaldehyde), which is then used in the manufacturing process. However, when formaldehyde is converted to such derivatives, the generation of unreacted formaldehyde components in the process is unavoidable. Unreacted components are typically discharged from the system as formaldehyde of low concentration (e.g. water-rich formaldehyde) and distilled or otherwise separated as described above, thereby producing formaldehyde of a higher concentration for further use. However, problems of high energy consumption and the need to use special corrosion-resistant materials as described above remain unsolved.

A similar problem occurs in the process proposed in U.S. Pat. No. 2,467,223 for producing formaldehyde by oxidizing methylal. The resulting formaldehyde is of low concentration and must be enriched before it can be of practical use.

It should also be noted that neither U.S. Pat. No. 2,467,223 nor JP-B-40-15005 discloses or suggests a one-step process for producing formaldehyde from methanol by combining a process for producing methylal from methanol and formaldehyde with a process for producing formaldehyde by oxidation of methylal. Neither patent refers to a technique for effectively recycling the dilute formaldehyde (formaldehyde of low concentration) which occurs in the recovery of highly concentrated formaldehyde or derivatives thereof.

SUMMARY OF THE INVENTION

An object, therefore, of the present invention is to provide a process for efficient and continuous production of highly concentrated formaldehyde or derivatives thereof from methanol via methylal.

Another object of the present invention is to provide a method by which dilute formaldehyde that results from the process of recovering highly concentrated formaldehyde or derivatives thereof can be effectively recycled without employing any special concentrating unit.

Still another object of the present invention is to provide a process for producing formaldehyde or derivatives thereof which includes a highly efficient unit process for methylal production that consists of the combination of a distillation tower and a plurality of reactors packed with a solid acid catalyst.

A further object of the present invention is to provide a process for producing formaldehyde or derivatives thereof which includes a highly efficient unit process for oxidizing methylal that employs a catalyst-packed tubular reactor.

A still further object of the present invention is to provide a process for producing formaldehyde or derivatives thereof which includes a stage at which the formaldehyde-containing product gas resulting from the step of methylal oxidation is converted with high efficiency to an aqueous formaldehyde solution by a new method of absorption.

These and other objectives of the present invention are apparent in the following detailed description of the present invention and the accompanying drawings.

The above-stated objectives of the present invention are attained a follows:

A process for producing formaldehyde or derivatives thereof from methanol comprising the steps of:
(i) heating methanol and formaldehyde in aqueous solution in the presence of an acidic catalyst to obtain methylal;
(ii) oxidizing the resulting methanol in the presence of an oxidation catalyst to obtain a formaldehyde gas;

(iii) absorbing the formaldehyde gas resulting from the oxidation reaction into water or into an aqueous formaldehyde solution to obtain an aqueous formaldehyde solution;

(iv) either separating the aqueous formaldehyde solution obtained in step (iii) into formaldehyde of a lower water content and formaldehyde of a higher water content (water-rich formaldehyde) and recovering the formaldehyde of a lower water content, or reacting said aqueous formaldehyde solution to form a derivative of formaldehyde, separating said derivative from unreacted water-rich formaldehyde and recovering said derivative; and (v) returning the water-rich formaldehyde separated in step (iv) to step (i) for further use as the formaldehyde component.

Figure 1:
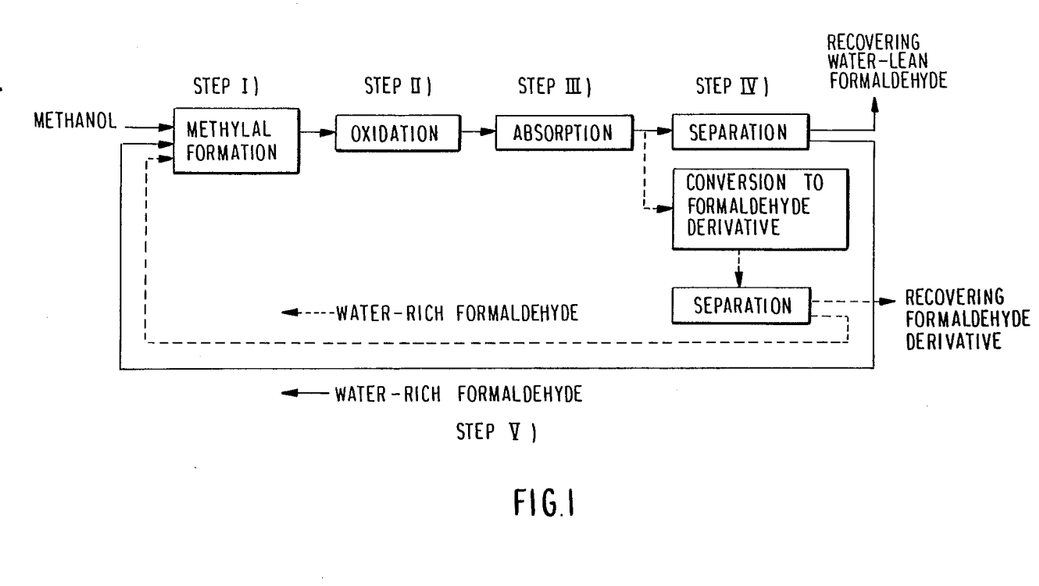
FIG. 1 is a flow diagram of a formaldehyde producing process according to one embodiment of the present invention.

A flow diagram of this embodiment of the present invention is shown in FIG. 1.

The process of the present invention is a two-step process in which methanol is first converted to methylal which then is oxidized to form formaldehyde. Theoretically, this method suffers a smaller loss of methanol due to its conversion to water than the method involving oxidation of methanol.

The present invention is further characterized in that the aqueous formaldehyde solution produced in this two-step process is separated into a formaldehyde component of low water content and a formaldehyde component of high water content, with the latter being recycled for effective use in the first stage of methylal formation. The unreacted formaldehyde component of high water content which results in the production of formaldehyde derivatives is similarly recycled for effective use in the first stage of methylal formation.

The process of the present invention is thus a recycle system using methanol as an input and which produces highly concentrated formaldehyde or a derivative thereof as an output, with formaldehyde of low concentration being repeatedly produced and consumed.

This technical concept of circulating formaldehyde of low concentration in the system was first discovered by the present inventors who recognized the new idea of combining two unit processes; one being the step of reacting methanol with formaldehyde to form methylal and the other being the step of oxidizing the resulting methylal to from formaldehyde. Therefore, the concept of the present invention could not have been obtained from either U.S. Pat. No. 2,467,223 or JP-B-40-15005 which only show the respective unit processes individually.

Besides the ability to produce highly concentrated formaldehyde or derivatives thereof from methanol in an efficient way, the process of the present invention has the added advantage that it does not require any special apparatus for concentrating the formaldehyde of low concentration which is inevitably produced in the system. By virtue of these advantages, the present invention successfully avoids the two major problems of the prior art, i.e., substantial energy consumption that would otherwise be required to operate a concentrating apparatus, and corrosion of the individual operating units of the system.

DETAILED DESCRIPTION OF THE INVENTION

The individual steps of the process of the present invention are described below in the order that they are performed.

(A) Synthesis of methylal from methanol and formaldehyde (Step of methylal formation):

It is known that methylal is synthesized from methanol and formaldehyde in the presence of an acidic catalyst through a condensation reaction expressed by the following equation;

$$2CH_3OH + CH_2O \rightleftharpoons CH_3OCH_2OCH_3 + H_2O.$$

As shown above, the synthesis of methylal from methanol and formaldehyde is a reversible reaction that yields water as a by-product.

This reaction proceeds over zinc chloride, ferric chloride, hydrochloric acid or any other acidic catalysts that are known to be usable in this type of reaction.

A preferred embodiment for methylal formation in accordance with the present invention is such that two or more reactors each packed with a solid acid catalyst are connected to a single distillation tower.

Stated more specifically, a solution containing methanol, formaldehyde and water is brought into solid-liquid contact with a solid acid catalyst and a methylal-rich component is recovered as a distillate. This process employs a distillation tower, and two or more reactors which communicate individually with the middle stage of the distillation tower and are each packed with the solid acid catalyst. In each of the reactors, a solution containing methanol, formaldehyde, water and the resulting methylal is circulated. The vapor in the distillation tower that undergoes gas-liquid contact with this solution after it has been subjected to solid-liquid contact in the reactor communicating with the lower side of the distillation tower is brought into another gas-liquid contact with the same solution which has undergone solid-liquid contact by circulation in the reactor communicating with a higher stage of the distillation tower. As the vapor is passed through successive stages of this gas-liquid contact, the concentration of methylal in the vapor phase is progressively increased.

According to this method, methylal is obtained in a yield of 95% or higher based on the formaldehyde feed.

Examples of the solid acid catalyst for use in the present invention include cation-exchange resins, sulfonated fluoroalkylene resin derivatives, and crystalline aluminosilicates.

Cation-exchange resins that can be used in the present invention may be carboxylated or sulfonated derivatives, but sulfonated derivatives are preferred because of the high reaction yield that can be attained. Ion-exchange resins that can be used may be gel-type cation-exchange resins or macroporous (macroreticular) cation-exchange resins, but the latter as exampflied by Amberlite 200C of Organo Co,, Ltd. and Lewatit SP112 of Bayer A.G. are preferred because of the high reaction yield that can be attained. Specific examples of useful ion-exchange resins include a styrene-divinylbenzene copolymer, an acrylic acid-divinylbenzene copolymer, a methacrylic acid-divinylbenzene copolymer, etc.

A sulfonated tetrafluoroethylene resin derivative (trade name, Nafion H) is preferably used as a sulfonated fluoroalkylene resin derivative.

Crystalline aluminosilicates for use as a solid acid catalyst in the present invention include those described in JP-A-58-162546 (the term "JP-A" as used herein means an "unexamined published Japanese patent application") which have a silica-to-alumina molar ratio of at least 10, and preferably 20 to 200. A preferred example is a mordenite-type crystalline aluminosilicate.

The most desirable of these solid acid catalysts are macroreticular cation-exchange resins having sulfonate groups.

The reactor for use in step (A) may be of any type so long as the solid acid catalyst is present in the column and if allows a solution containing formaldehyde and methanol to be brought into solid-liquid contact with the catalyst to form methylal. Examples of such reactors include vessels or towers in which the particles of a solid acid catalyst are tightly packed, vessels or towers in which the solid acid catalyst is dispersed in slurry form, and vessels or towers in which the particles of solid acid catalyst are loosely packed. The solution containing formaldehyde, methanol, water, and the resulting methylal is allowed to circulate in these reactors.

Figure 2:
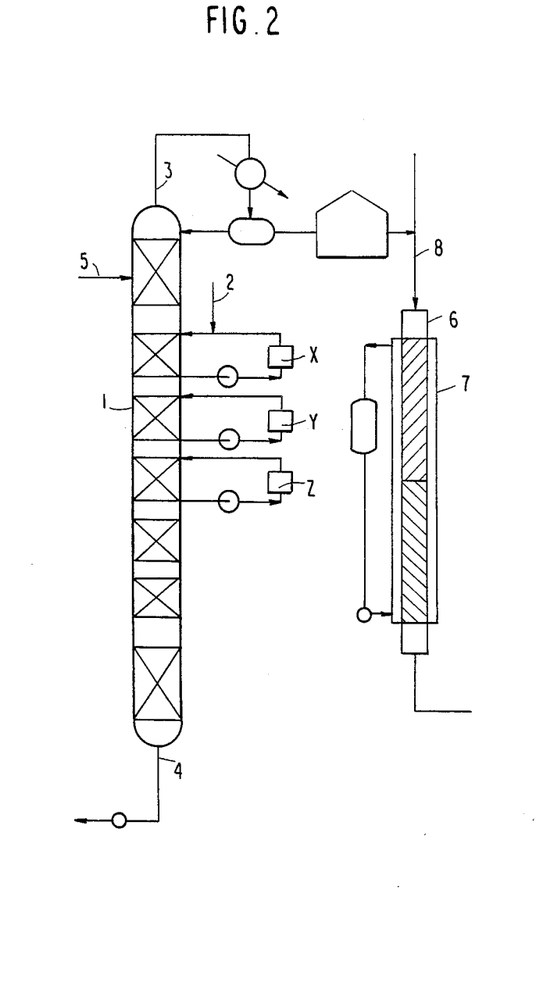
FIG. 2 is a flow scheme of the methylal synthesis and oxidation reaction described in the Referential Examples.

The type of reactor for use in step (A) which contains a solid acid catalyst and the mode of gas-liquid contact to be made between the methylal-containing vapor and the solution containing methanol, formaldehyde, water and the resulting methylal which has undergone solid-liquid contact with the solid acid catalyst are not limited in any particular way and an illustrative example is shown in FIG. 2.

In the process shown in FIG. 2, two feeds, i.e., an aqueous formaldehyde solution and methanol, are supplied to distillation tower 1 through feed pipes 5 and 2, respectively. Three reactor units X, Y and Z each packed with a solid acid catalyst are connected in that order to the middle stage of the distillation tower 1, with reactor unit X being in the highest position and Z being the lowest. In each of the reactor units, a solution containing methanol, formaldehyde, water and the resulting methylal is circulated by such means as a pump.

Consider the vapor in the distillation tower that undergoes gas-liquid contact with the solution that has been subjected to solid-liquid contact in reactor unit Y. The vapor then makes gas-liquid contact in the distillation tower 1 with the solution that has been brought into solid-liquid contact in reactor unit X, which communicates with the tower at a higher position, to form methylal. The reaction product, methylal, is discharged from the top of the tower 3, whereas unreacted methanol, formaldehyde and the water by-product are discharged from the bottom of the tower 4.

In step (A), an aqueous formaldehyde solution is chiefly used as the formaldehyde feed, but it may contain trioxane.

Methanol is normally used in an amount that is at least equal to its stoichiometric ratio to formaldehyde which is 2. Preferably, methanol is used in an amount of from 1.0 to 1.2 times this stoichiometric value, with the range of from 1.0 to 1.1 being particularly preferred. If an azeotropic mixture of methylal and methanol (92% methylal and 8% methanol) is to be obtained as a distillate, methanol is preferably used in an amount 1.1 times the stoichiometic value; if only methylal is to be obtained, methanol is preferably used in an amount equal to the stoichiometiric value; if a distillate intermediate between the two is to be obtained, methanol is preferably used in an amount of from 1.0 to 1.1 times the stoichiometric value.

In order to obtain methylal at a concentration of at least 95%, and especially at least 98%, the aqueous formaldehyde solution is preferably fed into the distillation tower at a position higher than any of the reactor units connected thereto so that it will make counter current gas-liquid contact with the methylal- and methanol-containg vapor ascending through the distillation tower.

In one embodiment of step (A), methanol is fed into the reactor that is connected to the distillation tower at the position (or stage) closest to the top. As the supplied methanol is allowed to circulate in that reactor, an aqueous formaldehyde solution is fed to a stage of the tower that is higher than the reactor supplied with methanol. In another embodiment, formaldehyde and methanol are fed into the reactor that is connected to the distillation tower at the position closest to its top. An aqueous solution containing formaldehyde is supplied to a feed stage that is higher in position that any of the reactors, so that the supplied aqueous solution is brought into countercurrent gas-liquid contact with the vapor ascending in the distillation tower which contains methylal and methanol. In this mode of operation, the solution in the reactor that is positioned closest to the top of the distillation tower may or may not be allowed to circulate. In the latter case, forced circulation is preferably effected in a reactor at a lower position in order to enhance the efficiency of the reaction.

In the step of methylal synthesis, it is normally preferred to employ at least three beds of solid acid catalyst. In some instances, 3 to 5 reactor units are used, and in other cases, 3 to 7 reactor units are employed.

The composition of the solution to be circulated in the reactor units usually consists of from 20 to 65 parts by weight of methanol, 0.001 to 20 parts by weight of formaldehyde, 34 to 79 parts by weight of water and 0.001 to 30 parts by weight of methylal, provided, however, that the concentration of each component varies with the position of each reactor unit.

The temperature in the reactor units is normally within the range of 45° to 90° C. but will slightly vary with the composition of the solution circulating in the reactor units and with the operating pressure in the distillation tower. Normally, the closer to the top of the distillation tower, the lower the temperature of the solution that is circulated in the reactor. For example, with seven reactor units, the operating temperature is in the ranges of 45° to 70° C., 55° to 75° C., 60° to 85° C., 65° to 85° C., 70° to 90° C., 7.0° to 90° C. and 70° to 90° C., the first-mentioned range being for the reactor unit positioned closest to the top of the distillation tower and the last-mentioned range being for the reactor unit positioned the farthest away from the top.

The distillation tower is operated either at atmospheric pressure or within the range of 1 to 3 atmospheres. Depending on the operating pressure, the temperature of the solution under circulation may sometimes reach 60° to 100° C.

The solution is circulated in the reactor units in an amount that normally ranges from 2 to 100 parts by weight, preferably from 25 to 50 parts by weight, per part by weight of the methylal vapor that is recovered as a distillate from the top of the distillation tower.

A solid acid catalyst of a strong acidic cationexchange resin is used in an amount of from 0.02 to 2 parts by weight for one reactor unit per part by weight of the methylal vapor to be recovered from the top of the distillation tower. The preferred range is from 0.05 to 1 parts by weight, which varies with the number of reactor units used.

The temperature at which each stage of the distillation tower is operated in the step of methylal formation depends on the number of reactor units used and the temperature of the solution circulating in each reactor unit. With four reactor units, the operating temperature of the distillation tower is within the ranges of 45° to 70° C., 55° to 75° C., 60° to 85°. C. and 65° to 90° C., the first-mentioned range being for the stage which communicates with the reactor unit positioned the closest to the top of the distillation tower, and the last-mentioned range for the stage which communicates with the reactor unit positioned the farthest away from the top. With five reactor units, the operating temperature of the distillation tower is in the ranges of 45° to 70° C., 55° to 75° C., 60° to 85° C., 65° to 90° C. and 70° to 90° C., and with six reactor units, the operating temperature is within the ranges of 45° to 70° C., 55° to 75° C., 60° to 85° C., 65° to 85° C., 70° to 90° C., and 70° to 90° C.

By employing the methods described above, an embodiment is possible wherein the purity of methylal distilling from the top of the distillation tower is adjusted to at least 98%, and the concentrations of methanol and formaldehyde in the water being discharged from the bottom of the tower are adjusted to 0.1% or lower.

In one preferred embodiment, distillation equipment may be employed in which 5 to 20 stages of distillation are provided between the reactor unit in the highest position and the top of the distillation tower, and at least 10 stages of distillation are provided between the reactor unit connected at the lowest position in the distillation tower and the bottom of the distillation tower.

In another embodiment, distillation equipment may be employed in which an aqueous solution of formaldehyde is supplied to a position at least three stages above the reactor unit in the highest position of the tower.

In a preferred embodiment for the operation of the distillation tower, the molar ratio of the distillate from the top of the distillation tower to the reflux to its top may be within the range of from 2:1 to 4:3.

In a certain preferred system, aqueous solutions containing formaldehyde of different concentrations are supplied to the distillation tower through two inlets such that the solution having the larger molar ratio of formaldehyde to water is fed together with methanol into the reactor units connected to the distillation tower whereas the solution having the smaller molar ratio of formaldehyde to water is fed to stages of the tower higher than the reactor units. In this case, trioxane may be present in the solution having the larger molar ratio of formaldehyde to water. Preferably, the composition of the aqueous solution having the larger molar ratio of formaldehyde to water is such that it consists of from 25 to 40 mol % of formaldehyde, 50 to 75 mol % of water, 0.2 to 1 mol % of trioxane and 3 to 10 mol % of methanol. The composition of the aqueous solution having the smaller molar ratio of formaldehyde to water is preferably such that it consists of 5 to 20 mol % of formaldehyde, 70 to 93 mol % of water and 2 to 15 mol % of methanol.

If desired, the aqueous solution having the larger molar ratio of formaldehyde to water may be supplied as a mixture with methanol to the reactor units connected to the distillation tower.

In step (A) of the process of the present invention, the solid acid catalyst can be readily separated from the solution containing unreacted methanol, formaldehyde, water, etc. With homogeneous catalysts such as sulfuric acid, separation from the reaction solution requires additional operations including distillation and neutralization, but these operations are not necessary in step (A).

A system having a plurality of reactor units are connected in communication with the distillation tower allows continuous operation for a prolonged period. Stated more specifically, the reactor units permit forced circulation of the feed. If backup reactor units are installed, some of the reactor units can be stopped for catalyst regeneration, change-out and recovery without discontinuing the production of methylal.

The methylal thus produced is transferred to the next step of oxidation where it is converted to formaldehyde gas.

(B) Synthesis of formaldehyde gas from methylal (Step of methylal oxidation):

In this step, formaldehyde gas is generated by oxidizing methylal in the presence of an oxidation catalyst. This method is described, for example, in U.S. Pat. No. 2,467,223.

Examples of the oxidation catalyst that can be used are also described in U.S. Pat. 2,467,223 and they include: silver, copper oxide, molybdenum, vanadium, iron molybdate, iron, molybdenum activated with manganese, magnesium, cadmium, calcium, etc., as well as phosphorus oxide and molybdenum oxide that are activated with manganese, magnesium, cadmium, calcium, etc. More preferred catalysts are those described in JP-A-57-134432 which contain as effective components iron, molybdenum and at least one metal element selected from among alkali metals, bismuth, chromium, tungsten, nickel and cobalt. These catalysts achieve high selectivity for formaldehyde with reduced production of carbon monoxide, dimethyl ether and methyl formate as co-products. As described in JP-A-60-251932, the proportions of the respective catalyst components are preferably such that molybdenum is 1.5 to 3.0 and the total amount of alkali metals, bismuth, chromium, tungsten, nickel and cobalt is 0.001 to 0.1 with respect to iron in terms of metal atomic ratio. Such catalysts have the added advantage of a long useful life.

In a preferred embodiment of step (B), formaldehyde gas is produced by oxidizing methylal using an oxide that contains as effective components iron and molybdenum or an oxide that contains as effective components iron, molybdenum and at least one metal element selected from among alkali metals, bismuth, chromium, tungsten, cobalt and nickel.

Specific examples of catalysts that can be used in step (B) include iron molybdate, a mixture of iron molybdate and molybdenum trioxide, and catalysts which additionally contain an oxide of at least one metal selected from among alkali metals, bismuth, chromium, tungsten, cobalt and nickel. The atomic ratio of molybdenum to iron (Mo/Fe) in these catalysts is normally within the range of 1.6 to 4.5, preferably 1.6 to 3.0, more preferably 1.6 to 2.5, and most preferably 1.6 to 1.9.

In a preferred embodiment, the oxidation catalyst is packed in tubular reactor units and a gas containing methylal and oxygen is allowed to flow through the catalyst bed to generate formaldehyde. The packed catalyst may be in the form of granules, cylinders, Rasching rings, spoke rings, etc.

In a preferred mode of catalyst packing, the oxide catalyst in the first entrance half of the tube has an atomic ratio of molybdenum to iron (Mo/Fe) of from 1.6 to 2.5, whereas the oxide catalyst in the second half of the tube has a Mo/Fe atomic ratio of from 1.6 to 4.5. It is particularly preferred that the first entrance half of the tube is packed with an oxide catalyst having a Mo/Fe atomic ratio of from 1.6 to 2.5 or 1.6 to 2.0 and the second half of the tube is also packed with an oxide catalyst having a Mo/Fe atomic ratio of from 2.0 to 4.5 or 2.0 to 3.5.

In the case of using tubular reactor units, it is more preferred that the concentrations of the methylal and oxygen to be supplied to the reactor units satisfy the following condition (1):

$$7.0 \geq X \geq 2.0$$

and $$1.04X - 3.9 \geq X \geq 1.04Y - 5.9 \quad (1)$$

where X is the volume % of gaseous methylal supplied to the reactor units, and Y is the volume % of oxygen supplied to the reactor units.

In step (B), the methylal feed may contain methanol. In the case where a gas containing methylal, methanol and oxygen is allowed to flow through the oxide catalyst bed to generate formaldehyde, the feed concentrations of methylal, methanol and oxygen preferably satisfy the following condition (2):

$$7.0 \geq X + Z/2 \geq 2.0$$

and $$(1.04/m)Y - 3.9 - 7.63(n/m) \geq X \geq (1.04/m)Y - 5.9 - 9.4(n/m) \quad (2)$$

X and Z are the volume % of gaseous methylal and methanol supplied to the reactors, respectively; Y is the volume % of oxygen supplied to the reactors; and X, Z, m and n satisfy the following relationships:

$m = 2X/(2X+Z)$,
$n = Z/(2X+Z)$ and $0.5 \geq n > 0$, $1 > m \geq 0.5$.

If the relationship between the concentration of oxygen to be supplied to the reactor units and the concentration of methylal and/or methanol satisfies condition (1) or (2), formaldehyde is stably produced. If, in condition (1) which sets forth the relationship between the concentration of methylal X(vol %) and the concentration of oxygen Y(vol %), the concentration of methylal exceeds $1.04Y - 3.9$, it is difficult to maintain the activity of reaction for an extended period. The selectivity for formaldehyde also tends to decrease with time, as evidenced by increased production of carbon monoxide as a by-product. If the concentration of methylal becomes lower than $1.04Y - 5.9$, the potential hazard of explosion will increase. The concentration of methylal in the vapor phase in contact with the catalyst bed is normally within the range of from 2 to 7 vol %, preferably 3 to 6 vol %, more preferably 4 to 5 vol %, and most preferably 4 to 4.5 vol %.

As described above, the concentrations of oxygen and methylal in the gas phase to be supplied to the reactor units must be controlled to lie within the ranges specified by condition (1) or (2). According to a preferred method that is commonly employed in the reaction production step (B), the reaction product which contains formaldehyde gas is prepared by mixing air and methylal with the oxygen-lean gas that is obtained by absorbing formaldehyde in a water-containing absorption tower.

The present inventors have found that when methylal either alone or in admixture with methanol is oxidized in an oxygen-containing vapor phase to produce formaldehyde, greater stable formaldehyde production can be achieved by performing the oxidation reaction of methylal over the catalyst under the conditions that satisfy the following relation:

[the rate of oxygen consumption per unit weight of catalyst]/[oxygen partial pressure] $\leq 1.0$ mol/hr·(g-catalyst)·(atm) \quad (3)

The "rate of oxygen consumption per unit weight of catalyst" in (3) means the number of moles of oxygen that are consumed in one hour of reaction per gram of catalyst, and the "oxygen partial pressure" is the partial pressure in atmospheres of oxygen in the reaction gas. The faster the rate of oxygen consumption, the faster the rate of oxidation reaction. It is difficult to determine directly the rate of oxygen consumption in a vapor-phase reaction, but it can be calculated on the basis of such factors including the increase in reaction temperature due to the heat of oxidation reaction, the specific heat and the flow rate of the reactants, and the heat balance between the reaction system (usually a tube is filled with a catalyst through which methylal or methylal-methanol mixed gas, oxygen, nitrogen, water and the reaction product will flow) and the outside of the system (which is usually a heat medium such as a molten inorganic salt or a heat-resistant organic medium). Oxygen partial pressure can also be calculated from such factors including the initial oxygen partial pressure prior to contact with the catalyst bed, the rate of oxygen consumption and the material balance of the reaction product.

In various calculations, the following values of the heat of reaction may be employed with advantage:

$$CH_2O + \tfrac{1}{2}O_2 \longrightarrow CO + H_2O$$
$$\Delta H = -56.52 \text{ Kcal/mol}$$

The rate of reaction and the chemistry of reaction can be calculated by simulating the reaction in the reaction system. This simulation is based on reaction analysis and the temperature distribution in the reaction system as determined from such factors including the overall heat transfer coefficient.

The value of [the rate of oxygen consumption per unit weight of catalyst]/[oxygen partial pressure] is preferably 1.0 or less, more preferably 0.7 or less, and most preferably 0.5 or less.

The value of [the rate of oxygen consumption per unit weight of catalyst]/[oxygen partial pressure] in the catalyst-filled tube correlates to the reaction temperature elevation curve. Stated more specifically, this value increases as the reaction temperature increases, and reaches a maximum just before the reaction temperatures peaks, and then decrease as the reaction temperature decreases. The maximum value of [the rate of oxygen consumption per unit weight of catalyst]/[oxygen partial pressure] is important and this is influenced by such factors as the temperature of heat medium, the concentration of methylal, the degree of catalyst dilution (the degree by which the catalyst is diluted with an inert substance) and the linear speed of reactants.

In a region where the value of [the rate of oxygen consumption per unit weight of catalyst]/[oxygen partial pressure] exceeds 1.0, molybdenum trioxide is reduced to yield black molybdenum dioxide as a by-product and it becomes difficult to perform the intended oxidation reaction for an extended period.

In step (B), the oxidation reaction of methylal or methylal-methanol mixed gas is normally performed in the temperature range of from 250° to 400° C. A preferred range is from 250° to 380° C., and a particularly preferred range is from 250° to 360° C. In a preferred embodiment, a gas containing methylal and oxygen is passed through the catalyst bed in the tube. Industrially employed reactor units are each composed of 5,000 to 50,000 tubes having an inside diameter of 15 to 25 mm and a length of 600 to 2,000 mm. The reaction temperature is controlled by passing a heat medium over the outside of the tubes within the reactor unit so that it will impart heat to, or remove heat from the reactants in the tubes.

Suitable heat media that can be used are inorganic salts, heat-resistant organic media, etc. The heat media are usually employed at temperature in the range of from 240° to 310° C. Normally, the temperature of heat media is raised as the reaction proceeds.

The linear speed of reactants in the reactor units is normally within the range of from 1.0 to 3.0 Nm$^3$/m$^2$·sec, more preferably 1.3 to 2.3 Nm$^3$/m$^2$·sec.

The conversion of methylal to formaldehyde in step (B) depends on the reaction conditions employed and is normally in the range of from 85 to 95%. As the reaction temperature decreases, the methylal conversion decreases. This is also the case when the reaction temperature is excessive because of the accurance of side reactions such as the formation of carbon monoxide.

(C) Absorption of the oxidation reaction product gas resulting from the step of methylal oxidation
(Absorption step):

The formaldehyde-containing gas obtained as the oxidation reaction product of step (B) is supplied to an absorption tower where it is absorbed into water or an aqueous formaldehyde solution.

Any type of absorption tower that is commonly employed in the art may be used and examples include packed towers or columns, towers provided with a plurality of trays, and wet-walled columns.

A countercurrent system is normally employed in the absorption tower, in which the formaldehyde-containing gas is introduced to the lower part or bottom of the tower, and an absorption medium is supplied to the top of the tower.

Water or an aqueous solution of formaldehyde may be employed as an absorption medium and in the latter case, an aqueous formaldehyde solution of high water content (e.g., 5 wt % or more) that will be separated in a subsequent step is preferably employed. Depending on the specific objective, the aqueous formaldehyde solution of low water content that is to be separated and recovered in the subsequent step may be employed as an absorption medium. An externally supplied separated aqueous solution of high or low water content may also be employed as an absorption medium. If desired, the water-rich aqueous solution of formaldehyde that has been obtained by direct oxidation of methanol is also suitable for use as an absorption medium.

In another preferred embodiment, the aqueous formaldehyde solution obtained from the bottom of the absorption tower is recycled to its top.

The quantity of water or aqueous formaldehyde solution to be used in the absorption step may be properly determined in accordance with the desired concentration of the aqueous formaldehyde solution that emerges from the absorption tower. Generally speaking, an aqueous formaldehyde solution is used as an absorption medium in a smaller amount than water.

Two absorption towers may be employed in one method for the absorption of formaldehyde gas. In one example of this method, the oxidation reaction product gas is absorbed into an aqueous formaldehyde solution of low concentration in the first absorption tower to obtain an aqueous formaldehyde solution of high concetration (e.g., 60 to 80 wt %) and part of the remaining oxidation reaction product gas, which is not absorbed in the first absorption tower, is absorbed into water or an aqueous formaldehyde solution in the second absorption tower to produce an aqueous formaldehyde solution of low concentration (e.g., 30 to 55 wt %, preferably 40 to 50 wt %) which is subsequently supplied to the first absorption tower. In another example, an aqueous formaldehyde solution of low concentration is sprayed using a spray nozzle in the first absorption tower. In either case, the second absorption tower is furnished with a filler or some other means for effecting gas-liquid contact.

A problem associated with the case where a high concentration of formaldehyde is present in said product gas is that formaldehyde will be easily deposited as scale and the chance of clogging of the absorption tower is increased. In order to solve this problem, the following method may be adopted when the formaldehyde-containing gas obtained by oxidation of methylal is absorbed into water or an aqueous formaldehyde solution: Before the formaldehyde-containing gas is supplied to the packing or trays in the absorption tower or to some other gas-liquid contact equipment, the water content of the gas is increased and only thereafter is the gas subjected to gas-liquid contact with the packing or trays in the absorption tower or a gas-liquid contact apparatus such as a wetted-wall column.

The reaction product gas obtained by oxidation of methylal usually has a water content in the range of 4 to 10 vol %. This water content is preferably elevated to at least 15 vol % before the gas is introduced into the absorption tower. A preferred method for increasing the water content of the formaldehyde-containing gas is to bring it into contact with the aqueous formaldehyde solution that emerges from the absorption tower. The temperature of this aqueous formaldehyde solution is preferably elevated before it is brought into contact with the formaldehyde-containing gas. When expressed mathematically, the following condition (4) is desirably satisfied:

$$1.02M + 9 \leq T \leq 1.02M + 19 \quad (4)$$

where M is the concentration in wt % of the aqueous formaldehyde solution, and T is the temperature in °C. of this solution.

The use of absorption towers is not the only method of absorption that can be employed in step (C). Other methods include: (i) bubbling the formaldehyde-containing gas into an aqueous solution in a bubbling vessel; and (ii) allowing he formaldehyde-containing gas to make countercurrent contact with an absorption medium in a tube.

As already mentioned, the concentration of the aqueous formaldehyde solution to be obtained as a result of absorption in step (C) can be appropriately adjusted in accordance with the relationship between the quantities of formaldehyde gas and absorption medium used. A preferred concentration of the aqueous formaldehyde solution is within the range of from 60 to 80 wt %, with the range of 65 to 75 wt % being more preferred.

(D) Separation of the aqueous formaldehyde solution (Separation step):

The aqueous formaldehyde solution obtained in step (C) is subsequently separated into formaldehyde having a higher water content and a lower water content than said aqueous solution. The formaldehyde of a lower water content is recovered as the end product from the system, whereas the formaldehyde of a higher water content is recycled to step (A) as a feed for methylal formation.

Any method that is well known in the art may be used as a separation technique in step (D). A preferred method is employed in Example 2 as follows: The aqueous formaldehyde solution is reacted with an alcohol such as polyethylene glycol, cyclohexanol or trimethylolpropane to form hemiacetal, which then is heated in a decomposing vessel to be separated into a water-lean formaldehyde gas and a water-rich aqueous formaldehyde solution.

The water-lean formaldehyde thus separated and recovered may be used, for example, as a material for the production of acetal homopolymers.

In the case where the aqueous formaldehyde solution obtained in step (C) is converted to a derivative such as trioxane, which then is recovered as the end product from the system, water-rich formaldehyde is separated as unreacted formaldehyde as described in Example 1. The separated water-rich formaldehyde is recycled to step (A) for further use in methylal formation. Besides trioxane, various formaldehyde derivatives may be obtained, including paraformaldehyde and the condensation product of phenol and formaldehyde.

The concentration of the water-lean formaldehyde is usually adjusted to a water content of not more than 5 wt %. The concentration of the water-rich formaldehyde is normally adjusted to a water content of 5 wt % or more, preferably 5 to 50 wt %, more preferably 10 to 45 wt %.

The following examples are given for the purpose of illustrating the process of the present invention as it relates to the preferred case of producing formaldehyde gas or trioxane which is to be used as a material for the manufacture of polyacetal resins.

The selectivity for formaldehyde and the conversion of methylal to formaldehyde in the oxidation step are calculated by the following formulae:

Selectivity=[formaldehyde produced] in moles/-{supplied 3[methylal] moles +supplied [methanol]moles—unreacted [methanol]moles}×100%

Conversion=[formaldehyde produced]in moles/-{supplied 3[methylal]moles +supplied[methanol]moles}×100%

REFERENTIAL EXAMPLE 1

An experiment was conducted using a distillation tower 1 and three reactor units X, Y and Z as shown in FIG. 2. Each of the reactor units X, Y and Z was filled with 300 cc of a macroreticular strong acidic cation-exchange resin (Amberlite 200C). A 40% aqueous formaldehyde solution (containing 1% methanol) was supplied through a feed pipe 5 at a rate of 200 g per hour, and methanol was supplied through a feed pipe 2 at a rate of 169 g per hour.

The distillation tower 1 was a packed tower having a height of 2.5 m. The middle portion of the distillation tower 1 was furnished with stages from which liquid components were withdrawn and pumped to the reactor units X, Y and Z. The liquid components were circulated to make solid-liquid contact with a catalyst. The reaction solutions containing the resulting methylal which emerged from the reactor units X, Y and Z were returned to the distillation tower 1, where they made gas-liquid contact with the vapor ascending from the bottom of the tower 4 to its top 3 so that the concentration of methylal would progressively increase. The reflux was returned to the top of the distillation tower 1 so as to hold the top temperature at 42° C. The distillate was withdrawn from the top 3 at a rate of 204 g per hour and reserved in a tank. The purity of methylal in the distillate 2 was 99%. An aqueous solution containing 0.5% formaldehyde and 0.01% methanol was discharged from the bottom 4 at a rate of 16.5 g per hour.

The resulting methylal was supplied to the oxidation reaction system employing an iron tube 6 (i.d., 21 mm; length, 100 cm) that was packed with an iron molybdate-molybdenum trioxide catalyst (Mo/Fe atomic ratio, 2.3) in the form of a spokes ring. The first 50-cm portion (the upper portion in FIG. 2) of the catalyst bed was composed of 75 vol % of the catalyst and 25 vol % of a ceramic Raschig ring. The second 50-cm portion (the lower portion in FIG. 2) of the catalyst bed was solely composed of the catalyst. An organic heat-resistant oil (trade name, SK Oil) was circulated at 260° C. over the outside of the tube 7. A gas consisting of 4 vol % methylal, 8.3 vol % oxygen, 2 vol % water and the balance nitrogen was supplied to the catalyst bed through a conduit 8 at a linear speed of 1.2 Nm$^3$/m$^2$·sec. A fine hollow syringe needle having an inside diameter of 1 mm and an outside diameter of 1.5 mm was inserted through the center of the catalyst bed in the tube from top to bottom and a thermocouple was passed through this needle for measurement of the temperature in the tube. Based on heat balance and reaction analysis, the value of [the rate of oxygen consumption per unit weight of catalyst]/[oxygen partial pressure] in the catalyst bed was determined. A maximum value of 0.44 mol/hr·(g-catalyst)(atm) was attained. The highest reaction temperature was 330° C.

The selectivity for formaldehyde from methylal was 94% and the conversion to formaldehyde was 93%. The amount of by-product carbon monoxide was 3% of the product formaldehyde.

The reaction product gas was then introduced into an absorption tower filled with a Dickson packing. The gas was bubbled into an aqueous formaldehyde solution in the bottom of the absorption tower. After the bubbling, the gas was brought into gas-liquid contact in the packed portion. Makeup water was fed to the absorption tower from it stop and its quantity was adjusted in such a way that the concentration of formaldehyde in the aqueous formaldehyde solution in the bottom of the absorption tower would be held at 65%.

REFERENTIAL EXAMPLE 2

The procedures of Referential Example 1 was repeated except that methylal synthesis was performed using the solid acid catalyst shown in Table 1 in place of the macroreticular cation-exchange resin (trade name, Amberlite 200C). The results of the oxidation and absorption steps were entirely the same as those obtained in Referential Example 1. The results of the methylal synthesis step are also given in Table 1.

REFERENTIAL EXAMPLE 3

The oxidation step of the process performed in Referential Example 1 was repeated using a tube filled with an annular iron-molbdenum oxide catalyst (atomic ratio of Mo/Fe=2.2) and with a heat-resisntant heat medium being circulated at 260° C. in the outside of the tube. A gas containing 8.5 vol % oxygen and 4.5 vol % methylal that satisified condition (1) was supplied to the catalyst bed at a liner speed of 1.5 Nm³/m²·sec. The supplied gas contained 2 vol % of water. Based on reaction analysis, the value of [the rate of oxygen consumption per unit weight of catalyst]/[oxygen partial pressure] in the catalyst bed was determined. A maximum value of 0.45 mol/hr·(g-catalyst)(atm) was attained.

The highest reaction temperature was 340° C. The conversion to formaldehyde was 92%. The amount of by-product carbon monoxide was 4% of the product formaldehyde. The results of the other steps were entirely the same as those obtained in Referential Example 1.

REFERENTIAL EXAMPLE 4

The procedures of Referential Example 1 were repeated using a Rasching ring of iron-molybdenum-chromium oxide catalyst (atomic ratio of Mo/Fe/Cr=2.1/1/0.02). The conversion to formaldehyde was 92%, and 3% CO was formed as a by-product. A maximum value of [the rate of oxygen consumption per unit weight of catalyst]/[oxygen partial pressure] as determined by reaction analysis was 0.45. The highest reaction temperature was 330° C. The results of the other steps were entirely the same as those obtained in Referential Example 1.

The oxidation step was continued for 3 months and the selectivity for formaldehyde remained at the initial 94%. The oxidation catalyst was withdrawn from the tube for examination; a black deposit of molybdenum dioxide was barely noticeable.

REFERENTIAL EXAMPLE 5

The procedures of Referential Example 1 were repeated with the heat medium circulated at 270° C. in the oxidation step. The value of [the rate of oxygen consumption per unit weight of catalyst]/[oxygen partial pressure] reached a maximum of 0.82 mol/hr·(g-catalyst)(atm). The highest reaction temperature was 380° C. The selectivity for formaldehyde from methylal was 92%. The results of the other steps were entirely the same as those obtained in Referential Example 1.

The oxidation step was continued for 3 months and 91% selectivity for formaldehyde was maintained. The catalyst was withdrawn from the tube for examination; a black deposit of molybdenum dioxide was observed.

TABLE 1

| Referential Example No. | Solid Acid Catalyst | Distillate from the top Methylal (%) | Extract from the Bottom Formaldehyde (%) | Extract from the Bottom Methanol (%) |
| --- | --- | --- | --- | --- |
| 2 | cation-exchange resin (gel type) (trade name, Amberlite 120 B) | 99 | 0.5 | 0.01 |
| 3 | Crystalline mordenite-type aluminosilicate (silicate-to-alumina molar ratio = 70) | 99 | 0.6 | 0.01 |
| 4 | Crystalline alumino-silicate (silica-to-alumina molar ratio = 10) | 99 | 0.6 | 0.02 |
| 5 | sulfonated tetrafluoroethylene resin derivative (trade name, Nafion H) | 99 | 0.6 | 0.02 |

EXAMPLES 1

Figure 3:
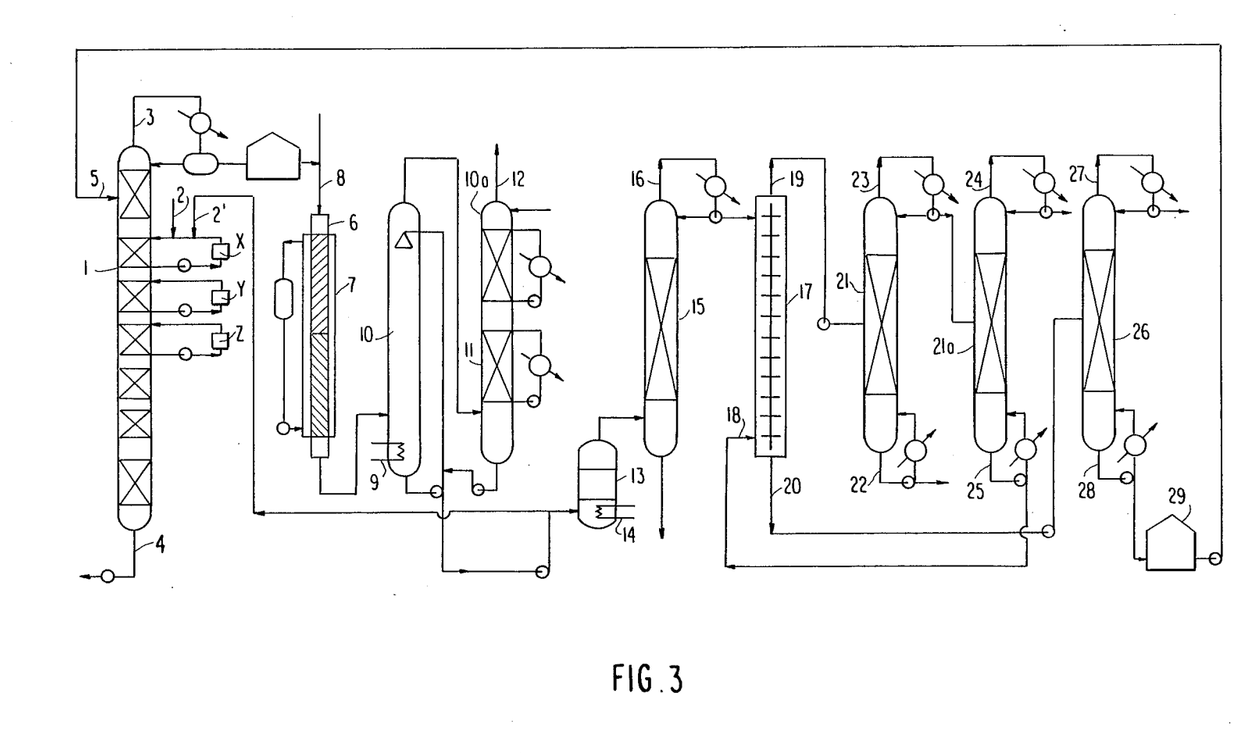
FIGS. 3 an 4 are flow schemes of a formaldehyde production process according to additional embodiments of the present invention.

Using the process shown in FIG. 3, trioxane which is a derivative of formaldehyde, were produced from methanol. Methylal synthesis was conducted using a distillation tower 1 and three reactor units X, Y and Z as shown in FIG. 3. Each of the reactor unit X, Y and Z was filled with 300 cc of a macroreticular strong acidic cation-exchange resin (trade name, Amberlite 200C). A 35% aqueous formaldehyde solution (containing 1% trioxane) was supplied through a feed pipe 5 at a rate of 188 g per hour. Methanol was supplied through a feed pipe 2 at a rate of 246 g per hour, and a 70% aqueous formaldehyde solution was supplied through a feed pipe 2' at a rate of 69 g per hour.

The distillation tower 1 was a packed tower having a height of 2.5 m. The middle portion of the distillation tower 1 was furnished with stages from which liquid components were withdrawn and pumped to the reactor units X, Y, and Z where they were circulated to make solid-liquid contact with a catalyst. The reaction solutions containing the resulting methylal which emerged from the reactor units X, Y and Z were returned to the distillation tower 1, where they made gas-liquid contact with the vapor ascending from the bottom of the tower 4 to its top 3 so that the concentration of methylal would progressively increase. The reflux was returned to the top of the distillation tower 1 so as to hold the top temperature at 42° C. The distillate was withdrawn from the top 3 at a rate of 295 g per hour and reserved in a tank. The purity of methylal in the distillate was 99%. An aqueous solution containing 0.5% formaldehyde and 0.01% methanol was discharged from the bottom 4 at a rate of 208 g per hour.

The resulting methylal was supplied to the oxidation reaction system employing an iron tube 6 (i.d., 21 mm; length, 100 cm) that was packed with an iron molybdate-molybdenum trioxide catalyst (Mo/Fe atomic ratio, 2.3) in the form of a spokes ring. The first 50-cm portion (the upper portion in FIG. 3) of the catalyst bed was composed of 75 vol % of the catalyst and 25 vol % of a ceramic Raschig ring. The second 50-cm portion (the lower portion in FIG. 3) of the catalyst bed was solely composed of the catalyst. An organic heat-resistant oil (trade name, SK Oil) was circulated at 260° C. over the outside of the tube 7. A gas consisting of 4 vol % methylal, 8.3 vol % oxygen, 2 vol % water and the balance nitrogen was supplied to the catalyst bed through a conduit at a linear speed of 1.7 $Nm^3/m^2 \cdot sec$. A fine hollow syringe needle having an inside diameter of 1 mm and an outside diameter of 1.5 mm was inserted through the center of the catalyst bed in the tube from top to bottom, and a thermocouple was passed through this needle for measurement of the temperature in the tube. Based on heat balance and reaction analysis, the value of [the rate of oxygen consumption per unit weight of catalyst]/[oxygen partial pressure] in the catalyst bed was determined. A maximum value of 0.42 mol/hr·(g-catalyst)(atm) was attained. The highest reaction temperature was 330° C.

The selectivity for formaldehyde from methylal was 94% and the conversion to formaldehyde was 92%. The amount of by-product carbon monoxide was 3% of the product formaldehyde.

The reaction product gas was then introduced into the first spray tower 10 that was equipped with a heater 9 to hold the solution temperature at 85° C. The introduced gas was converted to a highly concentrated aqueous formaldehyde solution in the spray tower 10. The gas leaving the spray tower 10 was introduced into the second absorption tower 10a and subjected to gas-liquid contact in the packed portion 11. Makeup water was supplied to the second absorption tower at an area close to its top 12, and the bottoms from the second absorption tower were supplied as spray water to the spray tower 10. The amount of makeup water supplied to the second absorption tower was adjusted in such a way that the concentration of formaldehyde in the aqueous formaldehyde solution in the bottom of the spray tower would be held at 70%. Example 1 employs a two-tower absorption system having the spray tower 10 and the second absorption tower 10a.

The resulting 70% aqueous formaldehyde solution (containing 1% methanol) was supplied both to a reactor 13 for trioxane synthesis and to the distillation tower 1 for methylal synthesis.

The 3-liters reactor 13 was supplied with the 70% aqueous formaldehyde solution (containing 1% methanol) at a rate of 386 g/hr. The reactor 13 contained 2% sulfuric acid. The contents of the reactor were boiled by means of a heater 14. The resulting trioxane-containing vapor was supplied to a 30-stage distillation tower 15. An aqueous solution containing 51% trioxane, 17% unreacted formaldehyde, and the remainder methanol, methyl formate, methylal, formic acid, etc. was withdrawn from the top 16 at a rate of 385 g/hr. The withdrawn aqueous solution consisting of trioxane, formaldehyde, etc. was supplied at a rate of 385 g/hr to the top of a 30-stage rotary disk extraction tower 17, which was supplied from the bottom 18 with benzene at a rate of 300 g/hr. A trioxane-benzene solution was withdrawn from the top 19 at a rate of 496 g/hr, and an aqueous solution containing 35% formaldehyde, 2% trioxane and 0.5% benzene was withdrawn from the bottom 20 at a rate of 190 g/hr. The trioxane-benzene solution was supplied to the middle stage of a distillation tower 21, where it was separated into high-purity trioxane and benzene by a commonly known method. The trioxane was withdrawn from the bottom 22 whereas the benzene was withdrawn from the top 23. The benzene was supplied to the middle stage of a subsequent distillation tower 21a, where methanol, methyl formate and other impurities in the benzene were further removed from the top 24. The purified benzene was recycled from the bottom 25 to the bottom 18 of the rotary disk extraction tower 17. The aqueous solution containing formaldehyde and trioxane that was withdrawn from the bottom 20 of the extraction tower 17 was supplied to the middle stage of another distillation tower 26, where a trace amount of benzene was removed from the top 27. An aqueous solution containing formaldehyde and trioxane was withdrawn from the bottom 28 at a rate of 188 g/hr and reserved in a tank 29. The concentration of formaldehyde in the withdrawn aqueous solution was 35%. The recovered aqueous formaldehyde solution was recycled to the distillation tower 1 for methylal synthesis.

EXAMPLE 2

Figure 4:
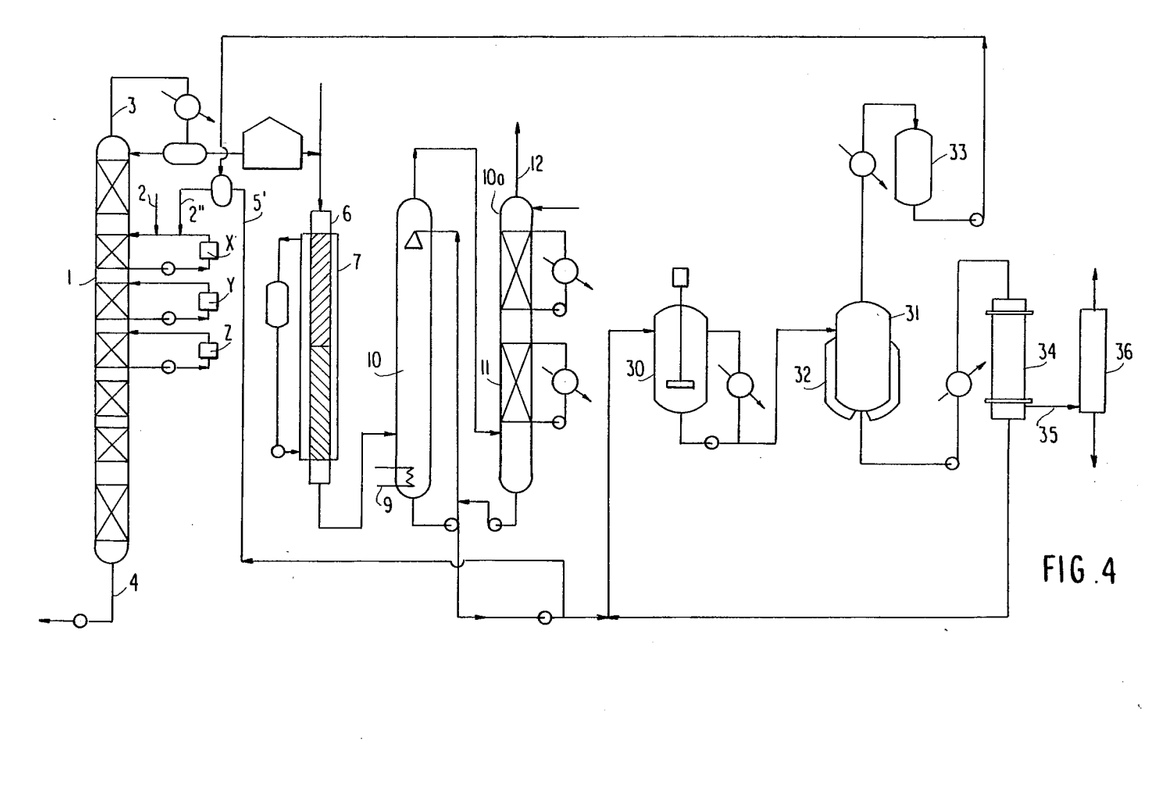

Using the process shown in FIG. 4, highly concentrated formaldehyde was produced from methanol. A 27% aqueous formaldehyde solution (containing 2% methanol) flowing at a rate of 170 g/hr was mixed with a 65% aqueous formaldehyde solution (containing 1% methanol) flowing at a rate of 76 g/hr and the mixture was supplied through a feed pipe 2" in the system shown in FIG. 4. Methanol was supplied through a feed pipe 2 at a rate of 225 g/hr. As in Referential Example 1, the distillation tower 1 for methylal synthesis communicated with three reactor units X, Y and Z and was operated in the same manner as in Referential Example 1. Methylal containing 10% methanol was recovered from the top 3 at a rate of 269 g/hr and reserved in a tank. The reaction water was withdrawn from the bottom 4.

The recovered methanol-containing methylal was then subjected to an oxidation step. The iron tube 6 used in this step was of the same type as the one employed in Referential Example 1 and the jacket 7 was similarly heated with a heat medium. The oxidation step was operated as in Referential Example 1 except that a gas consisting of 3.8 vol % methylal, 1.0 vol % methanol, 8 vol % oxygen, 2 vol % water and the balance nitrogen was supplied to the catalyst bed in the tube. Reaction analysis showed that the value of [the rate of oxygen consumption per unit weight of catalyst]/[oxygen partial pressure] reached a maximum at 0.45 mol/hr·(g-catalyst)(atm). The highest reaction temperature was 340° C.

The conversion of the methanol/methylal mixture to formaldehyde was 92%. The amount of by-product carbon monoxide was 3% of the product formaldehyde.

As in Example 1, the reaction product gas was introduced into a spray tower 10 for effecting gas-liquid contact. Makeup water was supplied to an absorption tower 10a in an area close to its top 12. With the temperature in the spray tower 10 held a 80° C. by means of a heater 9, the supply of makeup water was adjusted in such a way that the concentration of formaldehyde in its aqueous solution would be held at 65%. Part of the resulting aqueous formaldehyde solution was withdraw from the bottom of spray tower 10 and supplied through a conduit 5' both to the distillation tower 1 for methylal synthesis and to a hemiacetalizing vessel 30 for generating formaldehyde gas.

In the hemiacetalizing vessel 30, a 65% aqueous formaldehyde solution (containing 1% methanol) and hemiacetalized polyethylene glycol 400 were mixed at respective rates of 380 g/hr and 500 g/hr. The hemiacetalized reaction product was supplied to a vacuum dehydration vessel 31 at a rate of 880 g/hr. The vacuum dehydration vessel 31 was heated with a jacket 32 to remove moisture under vacuum. An aqueous solution of 27% formaldehyde distilled at a rate of 170 g/hr and was reserved in a container 33.

The dehydrated hemiacetal was supplied to a hemiacetal decomposing vessel 34 heated at 140° C. A crude formaldehyde gas containing 4% water was generated in the bottom 35 at a rate of 210 g/hr. The resulting formaldehyde gas was passed through a five-stage cooling trap 36 at 0° C. to obtain a pure gas of formaldehyde polymerization grade. Part of the hemiacetalized polyethylene glycol leaving the hemiacetal decomposing vessel 34 was returned as described above to the hemiacetalizing vessel 30.

EXAMPLE 3

In the absorption step of the process performed in Example 1, the aqueous formaldehyde solution withdrawn from the bottom of the absorption tower wa introduced into the discharge gas pipe from the oxidation reaction zone. Thus, the oxidation reaction product gas supplied to the absorption tower made gas-liquid contact with said aqueous formaldehyde solution. The liquid phase that had been subjected to gas-liquid contact was returned to the bottom of the absorption tower whereas the gas phase was subjected to another gas-liquid contact in the packed portion. The other operations were the same as those performed in Example 2. The system could be operated continuously for one week without causing any detectable scale deposition in the packed area of the absorption tower.

EXAMPLE 4

The aqueous formaldehyde solution at the bottom of the absorption tower was sprayed and circulated in that tower. The gas leaving the oxidation reaction step was supplied to the zone of spraying with the aqueous formaldehyde solution. The other operations were the same as those performed in Example 3. The system could be operated continuously for one week without causing any detectable scale deposition in the packed area of the absorption tower.

EXAMPLE 5

A spray tower was connected to the absorption tower. The gas leaving the oxidation reaction step was supplied to the spray tower. The oxidation reaction product gas emerging from the top of the spray tower was then introduced into the absorption tower. The bottoms from the absorption tower were supplied to the spray tower and circulated in it. The resulting aqueous formaldehyde solution was withdrawn from the bottom of the spray tower. The other operations were the same as those performed in Example 4. The system can be operated continuously for one week without causing any detectable precipitation of paraformaldehyde in the packed area of the absorption tower or in the produced aqueous formaldehyde solution.

EXAMPLE 6

A heater was installed at the bottom of the spray tower and the bottoms of the spray tower were circulated at a controlled temperature of 83° C. In addition, the concentration of formaldehyde in the aqueous formaldehyde solution obtained from the bottom of the absorption tower was adjusted to 65%. The other operations were the same as those performed in Example 1. The system could be operated continuously for one week without causing any detectable precipitation of paraformaldehyde in the packed area of the absorption tower or in the produced aqueous formaldehyde solution.

EXAMPLE 7

The procedures of Example 1 were repeated except that the temperature at the bottom of the spray tower was held at 85° C. and the concentration of formaldehyde in the produced aqueous formaldehyde solution was adjusted to 70%. The system could be operated continuously for one week without causing any detectable formation of paraformaldehyde in the packed area of the absorption tower or in the produced aqueous formaldehyde solution.

EXAMPLE 8

The gas leaving the oxidation reaction step was introduced into the bottom of the absorption tower as in Example 1 except that a 43% aqueous formaldehde solution prepared by silver-catalyzed oxidation of methanol was supplied to the top of the absorption tower in place of water. The oxidation product gas was bubbled in the absorption tower so that it made gas-liquid contact in the packed zone of the absorption tower. The supply of the 43% aqueous formaldehyde solution was adjusted in such a way that the concentration of the aqueous formaldehyde solution in the bottom of the absorption tower was 70%. The resulting aqueous formaldehyde solution was supplied to the reactor for trioxane synthesis. Excess aqueous formaldehyde solution was withdrawn from the system so as to attain material balance.

EXAMPLE 9

The procedures of Example 1 were repeated except that the supply of water to the absorption tower was adjusted in such a way that the concentration of the aqueous formaldehyde solution leaving the bottom of the absorption tower was 60%.

EXAMPLE 10

The 70% aqueous formaldehyde solution produced in Example 1 was dissolved in urea in such an amount that the molar ratio of formaldehyde to urea was 2:1 and water was subsequently evaporated. The aqueous solution obtained by condensation had a formaldehyde concentration of 7%. The recovered aqueous formaldehyde solution was added to a 70% aqueous formaldehyde solution to make a 40% aqueous formaldehyde solution which was then mixed with a 40% aqueous formaldehyde solution that had been separately prepared and fed to the distilation tower for methylal synthesis. The resulting mixture (40% aqueous formaldehyde solution) was supplied at a rate of 200 g per hour and treated as in Example 1 to prepare methylal. The methylal was then supplied to the oxygenator and the resulting oxidation reaction product gas was absorbed as in Example 1 to obtain a 70% aqueous formaldehyde solution.

EXAMPLE 11

The procedures of Example 1 were repeated except that the first half of the tube employed in the oxidation step was filled with an iron molybdate-molybdenum trioxide catalyst (atomic ratio of Mo/Fe=2.0) in the form of a spokes ring whereas the second half of the tube was filled with a similarly shaped iron molybdate-molybdenum trioxide catalyst (Mo/Fe atomic ratio=2.7). Based on heat balance and reaction analysis, the value of [the rate of oxygen consumption per unit weight of catalyst]/[oxygen partial pressure] in the catalyst bed was determined. A maximum value of 0.41 mol/hr·(g-catalyst)(atm) was attained. The highest reaction temperature was 330° C. The selectivity for formaldehyde from methylal was 95%, and the conversion to formaldehyde was 94%.

The process of the present invention is capable of producing highly concentrated formaldehyde or derivatives thereof from methanol in an efficient way It also has the added advantage that it does not require any special apparatus for concentrating the formaldehyde of low concentration which inevitably forms in the system. By virtue of these advantages, the present invention successfully avoids the two major problems of the prior art, i.e., substantial energy consumption that would otherwise be required to operate a concentrating apparatus and corrosion of the individual operating units of the system.

While the invention has been described in detail and with reference to specific embodiments thereof, it will be apparent to one skilled in the art that various changes and modifications can be made therein without departing from the spirit and scope thereof.

What is claimed is:

1. A process for producing formaldehyde or a derivative thereof from methanol, comprising the steps of:
   (i) heating methanol and formaldehyde in aqueous solution in the presence of an acidic catalyst to obtain methylal;
   (ii) oxidizing the resulting methylal using oxygen as an oxidizing agent in the presence of an oxide containing as effective components iron and molybdenum, or an oxide containing as effective components iron, molybdenum and at least one metal element selected from the group consisting of alkali metals, bismuth, chromium, tungsten, cobalt and nickel to obtain a formaldehyde gas;
   (iii) absorbing the formaldehyde gas resulting from the oxidation reaction into water or into an aqueous formaldehyde solution to obtain an aqueous formaldehyde solution;
   (iv) separating the aqueous formaldehyde solution obtained in step (iii) into formaldehyde of a lower water content and formaldehyde of a higher water content; and
   (v) returning the water-rich formaldehyde separated in step (iv) to step (i) for further use as the formaldehyde component, wherein said derivative of formaldehyde is selected from trioxane, paraformaldehyde, the condensation product of urea and formaldehyde and the condensation product of phenol and formaldehyde.

2. A process according to claim 1, wherein methylal is oxidized in step (ii) in the presence of methanol.

3. A process according to claim 1, wherein the step (i) employs a distillation tower and two or more reactors packed with a said acid catalyst that communicate individually with the middle stage of the distillation tower, and wherein a solution containing methanol, formaldehyde, water and the resulting methylal is circulated in each of said reactors, and wherein the vapor in the distillation tower that undergoes gas-liquid contact with the solution after it has been subjected to solid-liquid contact in the reactor communicating with the lower portion of the distillation tower is brought into another gas-liquid contact with the same solution which has undergone solid-liquid contact by circulation in the reactor communicating with a higher stage of the distillation tower, and wherein the concentration of methylal in the vapor phase is progressively increased as the vapor is passed through successive stages of gas-liquid contact.

4. A process according to claim 1, wherein the catalyst used in step (ii) is an oxide containing as effective components iron and molybdenum, said oxide catalyst being packed in a tube, and a gas containing both methylal or a mixture thereof with methanol and oxygen is passed through said catalyst bed to generate formaldehyde, and wherein the concentrations of methylal, methanol, and oxygen fed into the reaction system satisfy the following conditions:

$$7.0 \geq X + Z/2 \geq 2.0$$

and $$(1.04/m)Y - 3.9 - 7.63(n/m) \geq X \geq (1.04/m)Y - 5.9 - 9.4(n/m)$$

where X and Z are the volume % of gaseous methylal and methanol supplied to the reactors; Y is the volume % of oxygen supplied to the reactors; and m and n satisfy the following relationships:

$$m = 2X/(2X+Z)$$
$$n = Z/(2X+Z)$$

and $$0.5 \geq n > 0, \quad 1 > m \geq 0.5$$

5. A process according to claim 4, wherein the first entrance half of the tube is packed with a catalyst having a molybdenum-to-iron molar ratio (Mo/Fe) of from 1.6/1 to 2.5/1, and wherein the second half of the tube is packed with a catalyst having a molybdenum-to-iron molar ratio (Mo/Fe) of 1.6/1 to 4.5/1.

6. A process according to claim 1, wherein an oxide containing as effective components iron and molybdenum is used as the catalyst in step ii) for producing formaldehyde by oxidizing methylal or a mixture thereof with methanol in an oxygen-containing vapor phase, and wherein the oxidation reaction of methylal or a mixture thereof with methanol over said catalyst is performed under the conditions that satisfy the following reaction:

[the rate of oxygen consumption per unit weight of catalyst]/[oxygen partial pressure] $\leq 1.0$ mol/hr·(g-catalyst)·(atm)

wherein the "rate of oxygen consumption per unit weight of catalyst" is the number of moles of oxygen that are consumed in 1 hour of reaction per gram of catalyst, and the "oxygen partial pressure" is the partial pressure in atmospheres of oxygen in the reaction gas.

7. A process according to claim 1, wherein the concentration of water in the formaldehyde-containing gas produced in step (iii) is increased before it is supplied to the absorption tower for gas-liquid contact.

8. A process according to claim 7, wherein the water content of the resulting formaldehyde-containing gas is increased by bringing said gas into contact with the aqueous formaldehyde solution emerging from step (iii), said aqueous formaldehyde solution being heated before it is brought into contact with said gas under the following condition:

$$1.02M+9 \leq T \leq 1.02M+19$$

wherein M is the concentration in wt % of formaldehyde in the aqueous formaldehyde solution, and T is the temperature in °C. of the solution.

9. A process for producing formaldehyde or a derivative thereof from methanol, comprising the steps of:
  (i) heating methanol and formaldehyde in aqueous solution in the presence of an acidic catalyst to obtain methylal;
  (ii) oxidizing the resulting methylal using oxygen as an oxidizing agent in the presence of an oxide containing as effective components iron and molybdenum, or an oxide containing as effective components iron, molybdenum and at least one metal element selected from the group consisting of alkali metals, bismuth, chromium, tungsten, cobalt and nickel to obtain a formaldehyde gas;
  (iii) absorbing the formaldehyde gas resulting from the oxidation reaction into water or into an aqueous formaldehyde solution to obtain an aqueous formaldehyde solution;
  (iv) reacting the aqueous formaldehyde solution to form a derivative of formaldehyde, separating said derivative from unreacted water-rich formaldehyde, and recovering said derivative; and
  (v) returning the water-rich formaldehyde separated in step (iv) to step (i) for further use as the formaldehyde component, wherein said derivative of formaldehyde is selected from trioxane, paraformaldehyde and the condensation product of phenol and formaldehyde.

10. A process according to claim 9, wherein methylal is oxidized in step (ii) in the presence of methanol.

11. A process according to claim 9, wherein the step (i) employs a distillation tower and two or more reactors packed with a said acid catalyst that communicate individually with the middle stage of the distillation tower, and wherein a solution containing methanol, formaldehyde, water and the resulting methylal is circulated in each of said reactors, and wherein the vapor in the distillation tower that undergoes gas-liquid contact with the solution after it has been subjected to solid-liquid contact in the reactor communicating with the lower portion of the distillation tower is brought into another gas-liquid contact with the same solution which has undergone solid-liquid contact by circulation in the reactor communicating with a higher stage of the distillation tower, and wherein the concentration of methylal in the vapor phase is progressively increased as the vapor is passed through successive stages of gas-liquid contact.

12. A process according to claim 9, wherein the catalyst used in step (ii) is an oxide containing as effective components iron and molybdenum, said oxide catalyst being packed in a tube, and a gas containing both methylal or a mixture thereof with methanol and oxygen is passed through said catalyst bed to generate formaldehyde, and wherein the concentrations of methylal, methanol, and oxygen fed into the reaction system satisfy the following conditions:

$$7.0 \geq X + Z/2 \geq 2.0$$

and $$(1.04/m)Y - 3.9 - 7.63(n/m) \geq X \geq (1.04/m)Y - 5.9 - 9.4(n/m)$$

where X and Z are the volume % of gaseous methylal and methanol supplied to the reactors; Y is the volume % of oxygen supplied to the reactors; and m and n satisfy the following relationships:

$m = 2X/(2X+Z)$
$n = Z/(2X+Z)$ and $0.5 \geq n > 0 \quad 1 > m \geq 0.5$.

13. A process according to claim 12, wherein the first entrance half of the tube is packed with a catalyst having a molybdenum-to-iron molar ratio (Mo/Fe) of from 16/1 to 2.5/1, and wherein the second half of the tube is packed with a catalyst having a molybdenum-to-iron molar ratio (Mo/Fe) of 1.6/1 to 4.5/1.

14. A process according to claim 9, wherein an oxide containing as effective components iron and molybdenum is used as the catalyst in step (ii) for producing formaldehyde by oxidizing methylal or a mixture thereof with methanol in an oxygen-containing vapor phase, and wherein the oxidation reaction of methylal or a mixture thereof with methanol over said catalyst is performed under the conditions that satisfy the following reaction:

[the rate of oxygen consumption per unit weight of catalyst]/[oxygen partial pressure] $\leq 1.0$ mol/hr·(g-catalyst)·(atm)

wherein the "rate of oxygen consumption per unit weight of catalyst" is the number of moles of oxygen that are consumed in 1 hour of reaction per gram of catalyst, and the "oxygen partial pressure" is the partial pressure in atmospheres of oxygen in the reaction gas.

15. A process according to claim 9, wherein the concentration of water in the formaldehyde-containing gas produced in step (iii) is increased before it is supplied to the absorption tower for gas-liquid contact.

16. A process according to claim 15, wherein the water content of the resulting formaldehyde-containing gas is increased by bringing said gas into contact with the aqueous formaldehyde solution emerging from step (iii), said aqueous formaldehyde solution being heated before it is brought into contact with said gas under the following condition:

$$1.02M+9 \leq T \leq 1.02M+19$$

wherein M is the concentration in wt % of formaldehyde in the aqueous formaldehyde solution, and T is the temperature in °C. of the solution.

17. A process for producing formaldehyde or a derivative thereof from methanol, comprising the steps of:
(i) heating methanol and formaldehyde in aqueous solution in the presence of an acidic catalyst to obtain methylal;
(ii) oxidizing the resulting methylal using oxygen as an oxidizing agent in the presence of an oxide containing as effective components iron and molybdenum, or an oxide containing as effective components iron, molybdenum and at least one metal element selected from the group consisting of alkali metals, bismuth, chromium, tungsten, cobalt and nickel to obtain a formaldehyde gas,
(iii) absorbing the formaldehyde gas resulting from the oxidation reaction into water or into an aqueous formaldehyde solution to obtain an aqueous formaldehyde solution;
(iv) concurrently separating a portion of the aqueous formaldehyde solution obtained in step (iii) into formaldehyde of a lower water content and formaldehyde of a higher water content, and reacting the remaining portion of the aqueous formaldehyde solution to form a derivative of formaldehyde, separating said derivative from unreacted water-rich formaldehyde, and recovering said derivative; and
(v) returning the water-rich formaldehyde separated in step (iv) to step (i) for further use as the formaldehyde component, wherein said derivative of formaldehyde is selected from trioxane, paraformaldehyde and the condensation product of phenol and formaldehyde.

* * * * *

UNITED STATES PATENT AND TRADEMARK OFFICE
CERTIFICATE OF CORRECTION

PATENT NO. : 4,967,014

DATED : October 30, 1990

INVENTOR(S) : Junzo Masamoto et al

It is certified that error appears in the above-identified patent and that said Letters Patent is hereby corrected as shown below:

Claim 12, at col. 24, line 31, between "0" and "1", insert --,--.

Claim 13, at col. 24, line 35, delete "16" and inset --1.6--.

Signed and Sealed this

Ninth Day of February, 1993

Attest:

STEPHEN G. KUNIN

*Attesting Officer*  Acting Commissioner of Patents and Trademarks